United States Patent
Peleg

(10) Patent No.: US 11,937,996 B2
(45) Date of Patent: Mar. 26, 2024

(54) FACE CAPTURE AND INTRAORAL SCANNER AND METHODS OF USE

(71) Applicant: Align Technology, Inc., San Jose, CA (US)

(72) Inventor: Sharon Peleg, Hod Hasharon (IL)

(73) Assignee: Align Technology, Inc., San Jose, CA (US)

( * ) Notice: Subject to any disclaimer, the term of this patent is extended or adjusted under 35 U.S.C. 154(b) by 579 days.

(21) Appl. No.: 17/089,705

(22) Filed: Nov. 4, 2020

(65) Prior Publication Data

US 2021/0128281 A1 May 6, 2021

Related U.S. Application Data

(60) Provisional application No. 62/931,085, filed on Nov. 5, 2019.

(51) Int. Cl.
*A61C 9/00* (2006.01)
*A61B 1/00* (2006.01)
*A61B 1/24* (2006.01)
*A61C 7/00* (2006.01)

(52) U.S. Cl.
CPC .......... *A61C 9/006* (2013.01); *A61B 1/00172* (2013.01); *A61B 1/24* (2013.01); *A61C 7/002* (2013.01); *A61C 9/0066* (2013.01)

(58) Field of Classification Search
CPC ....... A61C 9/006; A61C 9/0066; A61C 7/002; A61B 1/00172; A61B 1/24
See application file for complete search history.

(56) References Cited

U.S. PATENT DOCUMENTS

| | | |
|---|---|---|
| 6,099,314 A | 8/2000 | Kopelman et al. |
| 6,334,772 B1 | 1/2002 | Taub et al. |
| 6,334,853 B1 | 1/2002 | Kopelman et al. |
| 6,463,344 B1 | 10/2002 | Pavlovskaia et al. |
| 6,542,249 B1 | 4/2003 | Kofman et al. |
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |

(Continued)

*Primary Examiner* — Nicholas D Lucchesi
(74) *Attorney, Agent, or Firm* — Shay Glenn LLP

(57) ABSTRACT

Apparatuses (e.g., systems, devices, etc.) and method for scanning both a subject's face as well as the subject's intra oral cavity to provide two-dimensional (2D) and/or three dimensional (3D) data that may be subsequently used in prosthodontic and orthodontic procedures, including smile planning (e.g., designing or modifying a subject's overall smile or facial aesthetics).

25 Claims, 7 Drawing Sheets

(56) References Cited

U.S. PATENT DOCUMENTS

| | | |
|---|---|---|
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,810,738 B1* | 10/2020 | Chen ............... G06T 19/00 |
| 10,813,727 B2 | 10/2020 | Sabina et al. |
| 10,839,481 B1* | 11/2020 | Chen ............... G06T 3/0075 |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 2010/0191510 A1* | 7/2010 | Kopelman ........... A61C 19/045 703/1 |
| 2011/0268327 A1* | 11/2011 | Getto ................ G09B 23/283 382/128 |
| 2012/0015316 A1* | 1/2012 | Sachdeva ............ G16H 40/20 382/128 |
| 2014/0170587 A1* | 6/2014 | Kopelman ......... A61B 1/00045 433/29 |
| 2014/0377714 A1* | 12/2014 | Jahn .................. A61C 1/084 433/29 |
| 2015/0037750 A1* | 2/2015 | Moalem ............. A61B 5/0088 433/29 |
| 2017/0273654 A1* | 9/2017 | Taguchi ............. A61B 6/035 |
| 2018/0110590 A1* | 4/2018 | Maraj ................ A61C 7/002 |
| 2019/0029784 A1 | 1/2019 | Moalem et al. |
| 2019/0046276 A1* | 2/2019 | Inglese .............. A61B 5/0088 |
| 2019/0167107 A1* | 6/2019 | Rohner .............. A61B 5/1079 |
| 2019/0350680 A1* | 11/2019 | Chekh ............... A61C 7/002 |
| 2019/0357997 A1* | 11/2019 | Shi .................... A61C 9/0046 |
| 2019/0388193 A1 | 12/2019 | Saphier et al. |
| 2019/0388194 A1* | 12/2019 | Atiya ................ G01B 11/2513 |
| 2020/0000551 A1* | 1/2020 | Li ..................... A61C 7/002 |
| 2020/0046460 A1* | 2/2020 | Jang .................. A61B 34/10 |
| 2020/0081413 A1* | 3/2020 | Georg ............... G05B 19/4099 |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349698 A1 | 11/2020 | Minchenkov et al. |
| 2020/0349705 A1 | 11/2020 | Minchenkov et al. |
| 2020/0404243 A1 | 12/2020 | Saphier et al. |
| 2021/0018579 A1* | 1/2021 | Nixdorf ............ G01R 33/34084 |
| 2021/0030503 A1 | 2/2021 | Shalev et al. |
| 2021/0045701 A1* | 2/2021 | Unklesbay .......... G06F 3/048 |
| 2021/0059796 A1 | 3/2021 | Weiss et al. |
| 2021/0068773 A1 | 3/2021 | Moshe et al. |
| 2021/0121049 A1 | 4/2021 | Rudnitsky et al. |
| 2021/0137653 A1 | 5/2021 | Saphier et al. |
| 2021/0196152 A1 | 7/2021 | Saphier et al. |
| 2022/0139044 A1* | 5/2022 | Koza ................. G06T 19/006 345/419 |
| 2022/0330911 A1* | 10/2022 | Schildkraut .......... A61B 6/466 |
| 2022/0338738 A1* | 10/2022 | Lee .................... H04N 13/218 |
| 2023/0062670 A1* | 3/2023 | Wang .................. A61C 7/08 |

* cited by examiner

603
Face scanning adaptor
optics

FACE CAPTURE AND INTRAORAL SCANNER AND METHODS OF USE

CROSS REFERENCE TO RELATED APPLICATIONS

This application claims the benefit of U.S. Provisional Patent Application No. 62/931,085, filed Nov. 5, 2019, titled "FACE CAPTURE AND INTRAORAL SCANNER AND METHODS OF USE," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatuses (e.g., systems, devices, etc.) and method for scanning both a subject's face as well as the subject's intra oral cavity to provide tow-dimensional (2D) and/or three dimensional (3D) data that may be subsequently used in prosthodontic and orthodontic procedures. In particular, the invention relates to such systems and methods that are computerized that may quickly and easily convert the system (e.g., a scanning wand) between face scanning and intraoral scanning.

BACKGROUND

In dental and orthodontic procedures it is beneficial to accurately and carefully measure the intraoral cavity, so that the dental procedure can be properly designed and any orthodontic appliances may be properly dimensioned to fit in place. In many cases, it may also be beneficial to have corresponding images of the face (e.g., lips, jaw, cheeks, eyes, etc.) in addition to the intraoral cavity. Having both images, and in particularly 3D models, of the subject's intraoral cavity and face may enhance the design of orthodontic and/or dental treatments, including predicting how treatments may impact both the subject's dentition as well as their overall aesthetics.

Previously described methods of scanning the intraoral cavity do not allow concurrent or sequential scanning of the subject's face in a single platform that is precise and easy to use. The apparatuses and methods described herein may address these deficiencies.

SUMMARY OF THE DISCLOSURE

The present invention relates to methods and apparatuses for using a wand of an intraoral scanner to scan both a subject's intraoral cavity as well as the subject's face. The subject's intraoral cavity is typically scanned to form a 3D model (e.g., a digital 3D model) of the intraoral cavity; the subject's face may be scanned to form one or more 2D images and/or in some variations a 3D image. These methods and apparatuses may store the intraoral cavity data (e.g., the scans and/or the 3D model of intraoral cavity) along with the face data (e.g., the scans and/or the 2D/3D model of the subject's face) as a single patient-specific data structure. Any appropriate scanning modality may be used, including confocal, structured light, etc.

In some variations it may be preferable to share optics for both the intraoral scanning and the facial scanning. For example, the sensor(s), lens(es), filter(s), etc., used for intraoral scanning may be adapted by additional optical components, e.g., lenses, filters, etc., that may extend the depth of focus from a depth that is appropriate to intraoral scanning, e.g., between 2-40 mm to a depth that is appropriate for using the same wand to scan the subject's face, e.g., 20-200 (e.g., 20-175 mm, 20-150 mm, 20-125 mm, 20-100 mm, 30-200 mm, 30-175 mm, 30-150 mm, 30-125 mm, 30-100 mm, 40-200 mm, 40-175 mm, 40-150 mm, 40-125 mm, 40-100 mm, etc.).

In some variations a control (e.g., switch, dial, button, knob, etc.) on the intraoral scanner, e.g., on the wand of the intraoral scanner, may be configured to switch between a first, intraoral scanning mode using a first optical path, and a second, facial scanning mode, either using a separate second optical path or using a second optical path to adapt the depth of focus of the first optical path.

In some variations a removable sleeve may include the second optical path for facial scanning, or for adapting the first optical path (the intraoral scanning optical path) for scanning the subject's face, e.g., by adjusting the depth of focus. For example, a removable sleeve may include lenses and/or other optical components (e.g., filters, mirrors, beamsplitters, prisms, diffraction gratings, etc.) forming the second optical path for imaging the subject's face. In particular, a removable sleeve may include a second optical path that modifies the first optical path (typically within the body of the wand) for intraoral scanning so that all or some of the sensors and/or optical components for intraoral scanning may be used for scanning the face.

Traditionally, dentist separately takes facial and dental still 2D images of the subject as part of new subject records. This process may involve using a separate camera (e.g., separate from the intraoral scanner), in some cases the second camera may be the physician's smartphone, and transmitting and/or storing these images as part of the patient's records. These images are flat (e.g., 2D) images. The methods and apparatuses described herein may generate, automatically or semi-automatically, a unified patient-specific data structure that include a 3D image of the patient's dentition (e.g., intraoral cavity) as well as facial images, which in some variations may be 3D face images. Thus the subject's face image(s) may be stored along with the intra oral 3D scans, allowing better integration of the data and future features for orthodontic or dental treatment planning, treatment monitoring and treating.

The methods and apparatuses described herein may also help in streamlining the process of treatment planning and design, monitoring and/or well as treatments. These methods and apparatuses may be performed without require the need to use and maintain additional device (e.g. camera) and/or for separately identifying the subject, capturing images, and/or uploading images.

In some variations, one or more calibration targets can be implemented, allowing the wand to measure and calibrate the optics and maintain the accuracy performance characteristics over time. For example in some variations the sleeves described herein may include one or more calibration targets.

Any of the sleeves described herein may be configured to fit over the wand. For example, a sleeve may be used a part of a protective sleeve for the wand, allowing calibration when the wand is not used and without any user involvement.

For example, described herein are methods comprising: scanning a subject's face with an introaroal scanner; and scanning the subject's intraoral cavity with the same intraoral scanner. Scanning the subject's face with the intraoral scanner may comprise passing light through a first optical path configured for intraoral scanning and a second optical path configured to adapt the first optical path for facial imaging. Any of these methods may include removing a sleeve having face-scanning optics configured to extend the depth of focus of the intraoral scanner. Scanning the subject's face with the intraoral scanner may comprise scanning using a first one or more sensors on the intraoral scanner, further wherein scanning the subject's intraoral cavity comprises scanning using a second one or more sensors on the intraoral scanner. In some variations, scanning the subject's face may comprise scanning with a depth of focus of between 20 mm and 200 mm (e.g., 20-175 mm, 20-150 mm, 20-125 mm, 20-100 mm, 30-200 mm, 30-175 mm, 30-150 mm, 30-125 mm, 30-100 mm, 40-200 mm, 40-175 mm, 40-150 mm, 40-125 mm, 40-100 mm, etc.), and wherein scanning the subject's intraoral cavity comprises scanning with a depth of focus of between 2 mm-40 mm (e.g., between 2-35, between 2-30, between 2-25, between 2-20, etc.).

Any of these methods may include actuating a control on a wand of the intraoral scanner to switch between scanning the subject's face and scanning the subject's intraoral cavity. Scanning the subject's face may include forming a 3D image of at least a portion of the subject's face, and/or scanning the subject's intraoral cavity may comprise forming a 3D image of at least a portion of the subject's intraoral cavity.

The scanning may occur in either order (e.g., scanning the subject's face first, or scanning the subject's intraoral cavity first). For example, the subject's intraoral cavity (e.g., teeth, gingiva, etc.) may be scanned before scanning the subject's face. Alternatively, in some variations, the subject's intraoral cavity may be scanned after scanning the subject's face. As described herein, scanning the subject's intraoral cavity may include scanning any portion of the subject's intraoral cavity, such as the upper jaw, lower jaw, certain teeth, etc. In some variations the intraoral scan may include separate scans of the upper and lower jaws (teeth, gingiva, etc.). Scanning the subject's face may include scanning all or a portion of the subject's face, such as the subject's mouth (lips, etc.) nose, cheeks, eyes, forehead, etc.

Any of these methods may include storing scan data from scanning of the subject's intraoral cavity with scan data from scanning the subject's face in a subject-specific data file, as mentioned. The scan data (2D and/or 3D) may include the raw scans, modified version of some or all of the raw scans (e.g., averaged, filtered, etc.), digital model(s) made from the scans (e.g., a digital model of the subject's upper and/or lower jaw, a digital model of the subject's face, etc.). The data from the facial scan and the data from the intraoral scan may be stored automatically to the patient-specific data file.

As mentioned, any scanning modality may be used for scanning the intraoral cavity and/or the patient's face. For example, scanning the subject's intraoral cavity may comprises scanning with structured light, confocal scanning, near-IR scanning, CT scanning, ultrasound scanning, optical coherence tomography, etc. Scanning the patient's face is typically done with visible light, and the same light source or a different light source may be used for scanning the intraoral cavity as for scanning the patient's face. In some variations the subject's face may be scanned with structured light, confocal scanning, etc.

As mentioned, in some variations, the method may include adapting the optical path used for intraoral scanning for face scanning. For example, a method may include: scanning a subject's face with an intraoral scanner, wherein scanning the subject's face comprises passing light through a first optical path configured for intraoral imaging and a second optical path configured to adapt the first optical path for facial imaging; and scanning the subject's intraoral cavity with the same intraoral scanner, wherein scanning the intraoral cavity comprises passing light through the first optical path but not the second optical path, wherein the second optical path increase the depth of focus of first optical path.

Any of these methods may include removing a sleeve having optics comprising the second optical path before scanning the subject's intraoral cavity. The first optical path may have a depth of focus of between 2 mm and 40 mm and the second optical path may adjust the depth of focus of the first optical path to be between 20 mm and 200 mm.

In any of these methods, scanning the subject's face may comprise forming a 3D image of at least a portion of the subject's face, and scanning the subject's intraoral cavity may comprise forming a 3D image of at least a portion of the subject's intraoral cavity. As mentioned, the scanning steps may be performed in any appropriate order. For example, the step of scanning the subject's intraoral cavity may be performed before scanning the subject's face. As mentioned, any of these methods may include storing scan data from scanning of the subject's intraoral cavity with scan data from scanning the subject's face in a subject-specific data file.

Also described herein are apparatuses (e.g., devices, systems, etc.) that are configured for performing any of the methods described. For example, an intraoral scanning system may include: a wand configured for intraoral scanning; a first optical path in the wand, the first optical path comprising one or more first optical path lenses and having a first depth of focus adapted for imaging the intraoral cavity; a second optical path on or in the wand, the second optical path comprising one or more second optical path lenses configured to provide a second depth of focus that is greater than the first depth of focus and is adapted for scanning a face; and a controller configured to receive intraoral scans from the first optical path and to receive face scans from the second optical path and to store data from the intraoral scan and data from a face scan in a subject-specific data structure. In any of these apparatuses, the wand may be configured to be hand-held.

In general, the first and/or second optical paths may include one or more lenses, mirrors, beamsplitters, prisms, diffraction gratings, etc. In some variations the first and/or second optical path includes one or more optical sensors (cameras, etc.). In some variations, the first and/or second optical path may include one or more light sources (e.g., laser light sources, etc.). For example, the first optical path may comprise a plurality of sensors in optical communication with the one or more first optical path lenses. As used herein the term "optical communication" means that light may be passed directly or indirectly between the components in optical communication (e.g., via an optical path).

In some variations the first and second optical path are separate (e.g., the first optical path is separate from the second optical path). In some variations, the first and second optical path are connected, so that the second optical path and the second optical path feed into each other (e.g., the second optical path feeds into the first optical path), so that face scanning path may share components with the intraoral scanner path. For example, the second optical path may be configured to be placed in line with the first optical path, and the second optical path lenses may be configured to extend the depth of focus of the first optical path.

In some variations, the system may include a control configured to switch between intraoral scanning using the first optical path and face scanning using the second optical path. The control may be a button, knob, handle, switch, etc. The control may be located on the wand and/or a region of the wand configured to be held.

Any of these devices may include a removable sleeve configured to at least partially cover the wand; as mentioned, the second optical path may be present on (including in or partially in) the removable sleeve.

The second optical path may exit the wand from a location that is different from the first optical path. For example, the second optical path may be on the front face of the wand (e.g., the distal-most face) or the back of the wand, opposite from the side of the wand used for intraoral scanning.

As mentioned above, in some variations the first optical path may have a depth of focus of between 2 and 40 mm (e.g., between 2-35, between 2-30, between 2-25, between 2-20, etc.). The second optical path may be configured to provide a depth of focus of between 20 and 200 mm (e.g., between 20-175 mm, 20-150 mm, 20-125 mm, 20-100 mm, 30-200 mm, 30-175 mm, 30-150 mm, 30-125 mm, 30-100 mm, 40-200 mm, 40-175 mm, 40-150 mm, 40-125 mm, 40-100 mm, etc.).

The wand may be configured for any appropriate imaging modality for intraoral and/or facial scanning (e.g., intraoral scanning by structured light, confocal scanning, etc.). For example, the wand may be configured for intraoral scanning by confocal scanning.

As mentioned, in some variations the apparatuses described herein are configured so that a sleeve (e.g., protective sleeve) may include a second optical path for facial scanning. In some variations the second optical path may be configured to adapt the intraoral scanning optical path (e.g., a first optical path) for facial scanning. For example, an intraoral scanning system may include: a wand configured for intraoral scanning comprising one or more lenses forming a first optical path having a depth of focus adapted for imaging the intraoral cavity; and a sleeve comprising a second optical path having one or more lenses configured to extend the depth of focus of the first optical path for scanning a face. The sleeve may be configure to be removably placed over the wand. In some variations the sleeve may include its own light source and/or sensors and may therefore be adapted to receive power, e.g., from a connection on the wand.

In general, the systems described herein may include a controller configured to receive intraoral scans and to store data from an intraoral scan and data from a face scan in a subject-specific data structure.

The first optical path may have a depth of focus of between 2 and 40 mm (e.g., between 2-35, between 2-30, between 2-25, between 2-20, etc.). The second optical path may be configured to provide a depth of focus of between 20 and 200 mm (e.g., between 20-175 mm, 20-150 mm, 20-125 mm, 20-100 mm, 30-200 mm, 30-175 mm, 30-150 mm, 30-125 mm, 30-100 mm, 40-200 mm, 40-175 mm, 40-150 mm, 40-125 mm, 40-100 mm, etc.).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6A shows a top perspective view, FIG. 6B shows a side view and FIG. 6C shows a bottom view.

DETAILED DESCRIPTION

In general, described herein are methods and apparatuses for scanning both a subject's face to get a digital model (e.g., 2D and/or 3D digital model) of the face and of the subject's oral cavity (e.g., teeth) with the same intraoral scanner, and in particular with the same wand of an intraoral scanner.

Figure 1A:
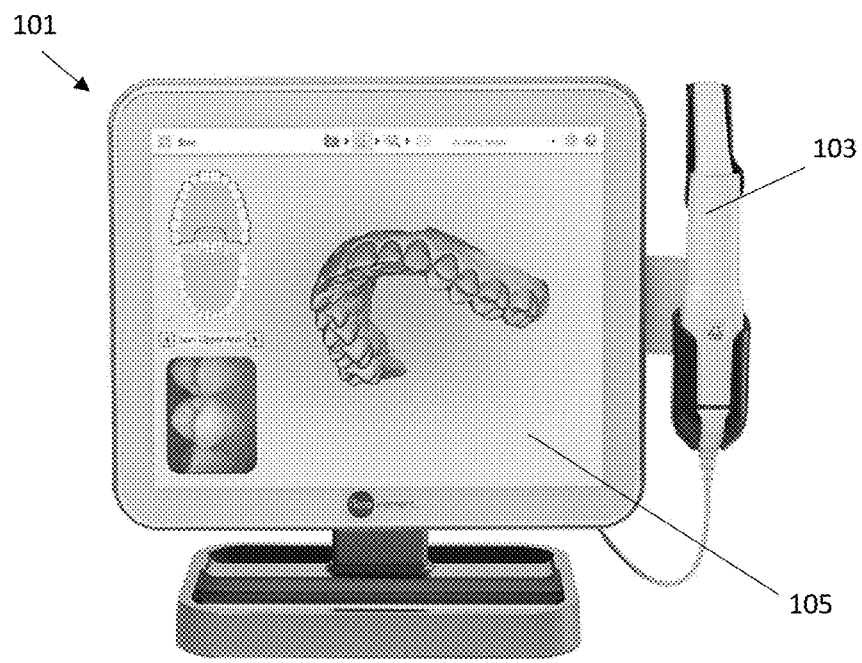
FIG. 1A illustrates one example of an intraoral scanner that may be adapted for used as described herein to perform both intraoral and facial scanning with the same wand of the intraoral scanner.

An intraoral scanner may generally include a wand and a controller, which may include a processor. For example, FIG. 1A illustrates one example of an intraoral scanner 101 that may be configured or adapted as described herein to scan both intraoral (e.g., internal features from a subject's oral cavity) and the subject's face. An intraoral scanner may include a handle or wand 103 that can be hand-held by an operator (e.g., dentist, dental hygienist, technician, etc.) and moved over a subject's tooth or teeth to scan intraoral structures. The wand may include one or more sensors (e.g., cameras such as CMOS, CCDs, detectors, etc.) and one or more light sources.

Figure 1B:
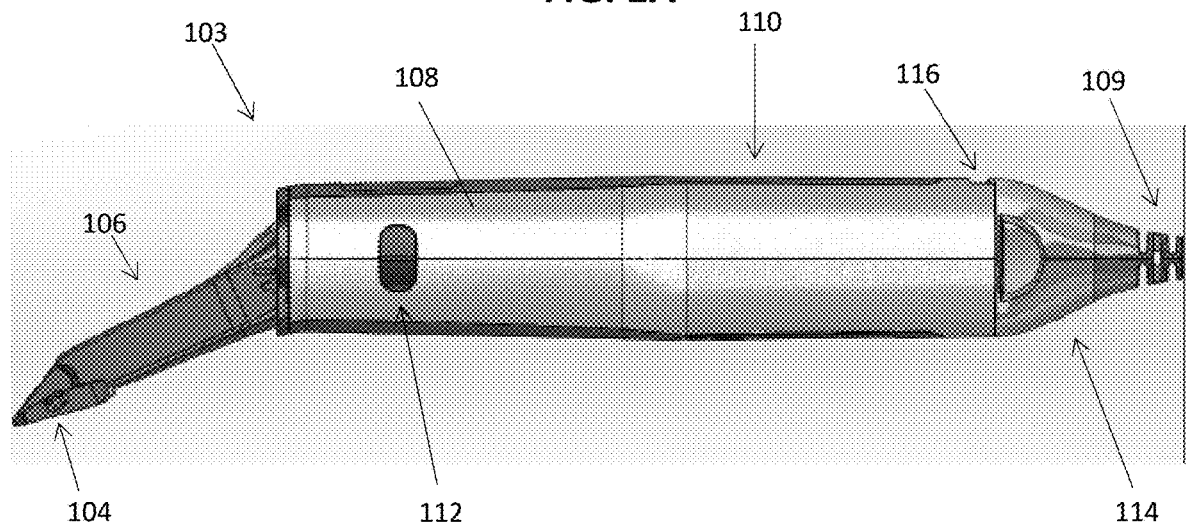
FIG. 1B is an example of one variation of a wand of an intraoral scanner as described herein.

FIG. 1B, shows an example of one variation of a wand 103. The wand may include one or more light sources configured to emit light (e.g., white light between 400-700 nm, e.g., approximately 400-600 nm, near-IR light, etc.). Separate illumination sources may be used. The light source may be any appropriate light source, including LED, fiber optic, etc. The wand 103 may include one or more controls (buttons, switching, dials, touchscreens, etc.) 112 to aid in control (e.g., turning the wand on/of, switching between scanning modes, etc.); alternatively or additionally, one or more controls, not shown, may be present on other parts of the intraoral scanner, such as a foot petal, keyboard, console, touchscreen 105, etc.

The wand may include an enclosure or housing that can include internal optical components for taking images of the subject's dentition. The intraoral scanner in FIG. 1A may be configured to take both intraoral scans and facial scans, and may be a handheld scanner that a practitioner can hold and maneuver by hand. In some embodiments, the scanner 100 is connected to a power source (not shown) and/or computer via one or more cables (e.g., wires or cords). In some embodiments, the scanner is configured to send data to a display that displays images of the patient's dentition and/or face collected by the scanner. In some cases, the scanner is configured to take two-dimensional and/or three-dimensional images of the dentition and/or face. In some embodiments, the scanner has its own power supply (e.g., battery) and/or wirelessly communicates with a processor.

The enclosure of the wand an include a main body 108 and a scanning portion 106, which includes one or more optical components 104 (e.g., optical window) that transmit optical signals to and/or from the internal optical components. The scanning portion 106 or probe that can have a shape and size adapted to maneuver around the patient's dentition and position an optical component 104 with respect to the patient's dentition and/or face. In some embodiments, the scanning portion 106 is at a distal end of the scanner 101 with the one or more optical component 104 at one side of the scanning portion 106. In some cases, at least part of the scanning portion 106 may enter into or come near the patient's mouth during an intraoral scanning operation. The scanning portion 106 can be connected to a main body 108 at a non-parallel angle to provide better access and maneuverability around the patient's dentition. The main body 108 can include a handle 110 that is sized and shaped for a practitioner to hold by hand. The main body 108 can include one or more controls 112 (e.g., actuators, buttons, switches, touchpads and/or sliders) for activating one or more functions of the scanner. In some cases, the main body includes one or more vents 116 (e.g., openings) that allow airflow to and from a ventilation component in the internal chamber of the scanner 101 for cooling the internal components of the scanner. In some cases, a proximal end of the main body 108 tapers at cable interface region 114 that couples the cable 109 to the main body 108.

The wand 103, and particularly the scanning portion may include a first optical path for scanning the intraoral cavity, e.g., teeth gingiva, etc. The first optical path may include one or more lenses, and a sensor configured to receive images of the teeth gingiva, etc. The focal depth may for the first optical path may be relatively close to the wand, for scanning within the intraoral cavity (e.g., the mouth), including scanning the teeth, for example between 1 and 40 mm (e.g., between 2-40 mm, etc.). Although the wand variation shown in FIG. 1B includes both a scanning portion 106 and a handle portion 110, in some variations the handle and scanning portion may be integrated to form an integrated, uniform portion or housing. In FIGS. 1A and 1B the wand is attached to other portions of the intraoral scanner by a cord; in some variations the wand may be cordless, and/or may include some or all of the processor, power supply, etc. within the same housing of the wand. For example, the apparatus may be configured to perform some processing, may be configured to perform all of the processing and/or may be configured to combine or share processing with the base unit.

Figure 2A:
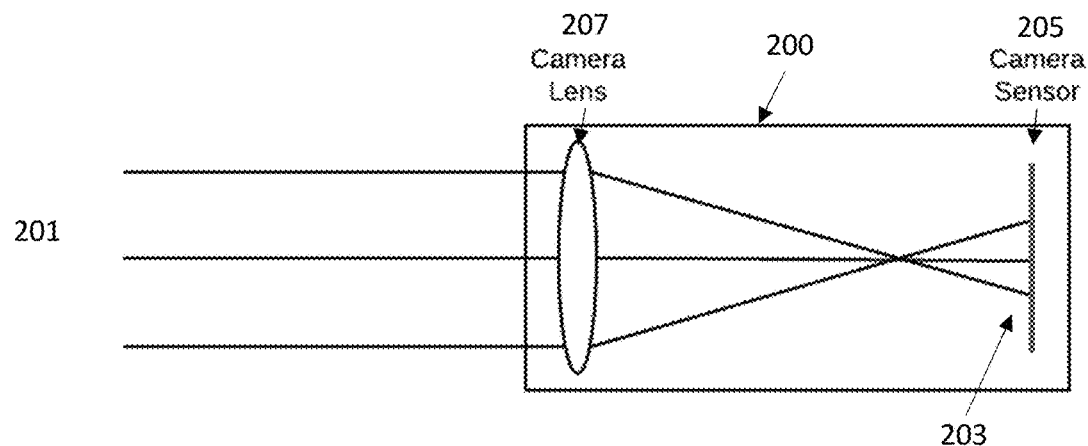
FIG. 2A schematically illustrates a first example of an optical path, e.g., a first optical path, that is configured to scan near-field (e.g., intraorally, within 2-40 mm, e.g., within 2-20 mm, etc.), but for which far-field (e.g., >20 mm) is out of focus.

In some variation, the wand may be configured switch between intraoral scanning and face scanning. For example, the wand may be configured to scan the patient's face before, during or after scanning the intraoral cavity. For example, FIG. 2A shows one example of the far field of view of an apparatus (e.g., an intraoral scanner) having a first optical path 200 that is configured to image within the near field of view. In FIG. 2A, the far field of view 201 is significantly out of focus, as shown 203; the camera lens 207 and camera sensor 205 are arranged so that features with the near field (e.g., between 1 mm and 40 mm, between 1 mm and 30 mm, between 1 mm and 20 mm, between 2 mm and 40 mm, between 2 mm and 30 mm, between 2 mm and 20 mm, etc.) are focused on the sensor 205, while objects further away (e.g., in the far field (e.g., between 20-200 mm, between 30-200 mm, between 40-200 mm, between 20-100 mm, between 30-100 mm, between 40-100 mm, greater than 20 mm, greater than 30 mm, greater than 40 mm, etc.) are out of focus.

Figure 2B:
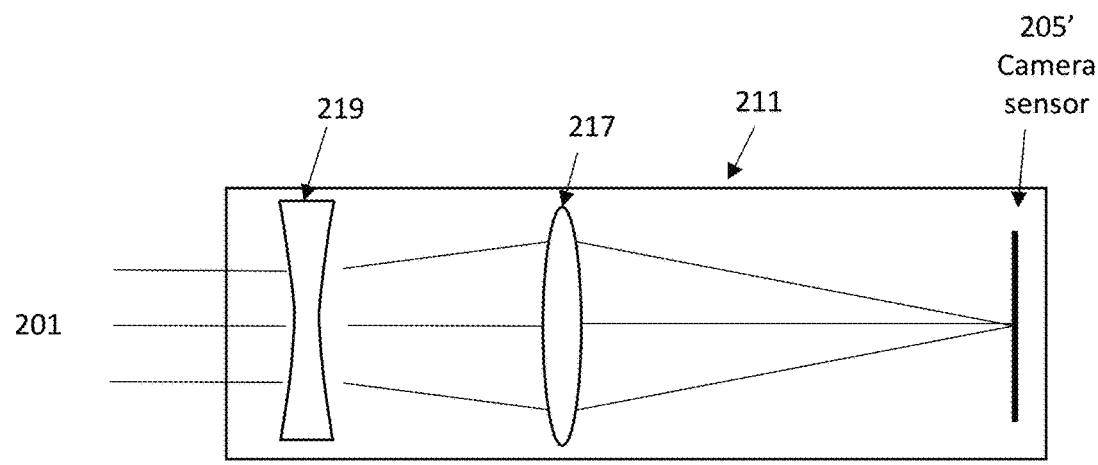
FIG. 2B shows an example of a second optical path that is configured to scan far-field (e.g., facial scans, within 20-200 mm).
Figure 2C:
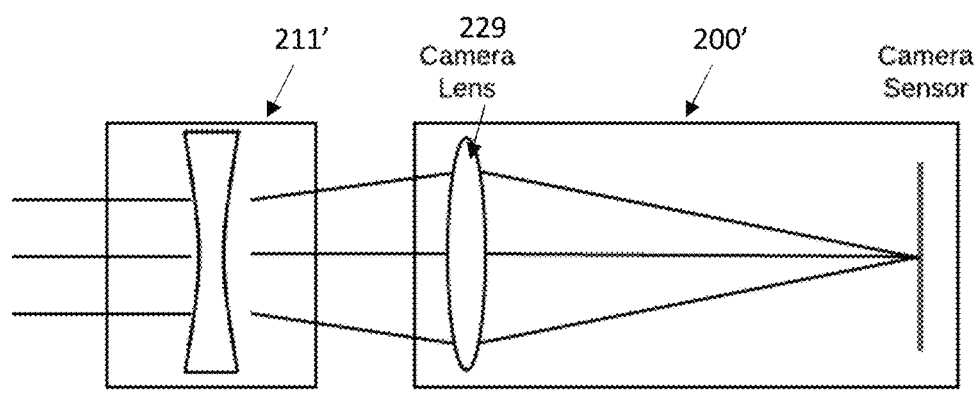
FIG. 2C shows an example of a second optical path that is in-line with a first optical path; the second optical path may be separate from the first optical path (which is configured to image near-field) and may adapt the first optical path to convert it to imaging far-field.

In some variations, as shown in FIG. 2B, a separate (e.g., second) optical path 211 may be included as part of the intraoral scanner, including as part of the wand. The second optical path may include optical elements that focus the far field 201 on a camera sensor 205'; the second optical path therefore includes one or more lenses 217, 219 arranged to focus the far-field 201 the sensor 205'. In FIG. 2B, the second optical path may be entirely separate from the first optical path, including the separate camera sensor 205', lenses 219, 217, etc. In some variations all or some of the same optical path elements (e.g., camera, lenses, etc.) may be shared between the first optical path (the near-field optical path for intraoral scanning) and the second (e.g., far-field optical path for facial scanning). For example, in FIG. 2C, the first optical path 200' may be in-line with a second optical path 211' so that the first optical path includes components (e.g., lenses 229, etc.) that may be modified by the second optical path so that the depth of focus is adjusted from the depth of focus for intraoral scanning (e.g., between 2-20 mm) to a depth of focus for facial scanning (e.g., 20-200 mm). In FIG. 2C, the far field of view of the apparatus (camera) with the second optical path 211' results in a far field of view that is in focus. In some variations more than one sensor and/or optical components may be used to scan either or both the intraoral scanning and/or the facial scanning. In some variations, as will be described in greater detail below, the second optical path may be part of a device that is removably coupled to the wand, such as a sleeve or cover.

Figure 3A:
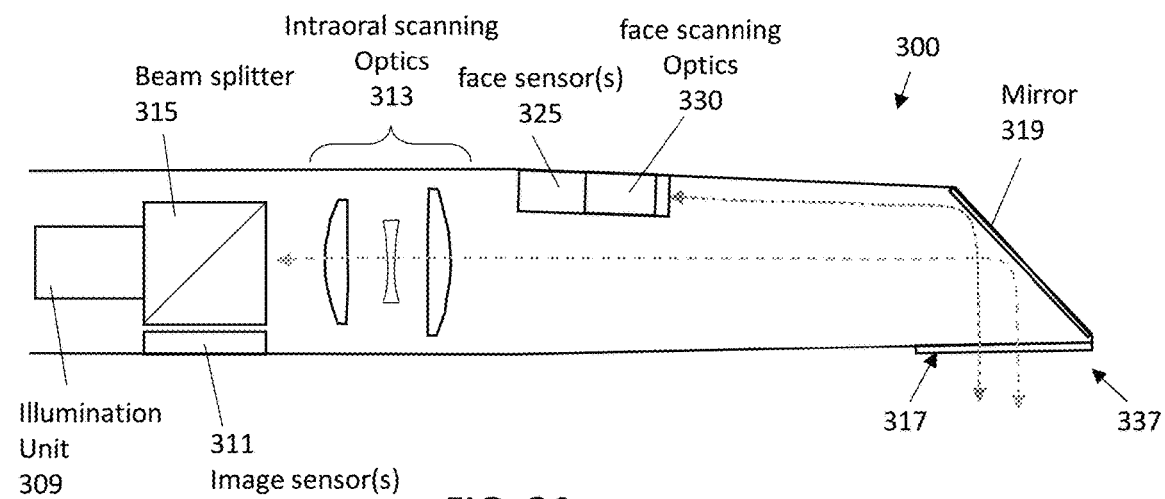
FIG. 3A shows a schematic through a portion of an intraoral scanner configured to perform both intraoral scanning (e.g., visible light, near IR, etc.) and facial scanning using the same wand.

FIG. 3A shows one example of a section through a portion of a wand (e.g., a scanning portion) of an intraoral scanner that is adapted for scanning both an intraoral cavity and a subject's face. In FIG. 3A, the scanner includes an illumination light 309 and a first optical path; the first optical path may include an image sensor 311, and additional optical elements, such as filters or polarizers. In the example shown in FIG. 3A, the wand also includes beam splitter 315. The first optical path in this example may also include first path scanning optics 313 (e.g., one or more lenses). The illumination unit (e.g., light, such as white light, laser, etc.) 309 may illuminate the field of view to be imaged, including the teeth, face, etc., in light wavelength appropriate for imaging. In some variations the illumination unit may be an LED and/or a laser. The same illumination source may be used for the first and second optical path, e.g., for both intraoral scanning and/or facial scanning. Alternatively, in some variations, a separate light source (e.g., LED) may be used for the second optical path. The first and/or second optical path may be used to image one or more imaging modality, including visible light, near-IR light, or different wavelengths of light, etc. In some variations the first and/or second optical path may extend down the interior of the wand 300 and be directed out of the side and/or end of the wand (exit region 317), e.g., steered by one or more mirrors 319.

In FIG. 3A, a second optical path may include a separate sensor (e.g., face sensor 325) and additional or separate optics (e.g., face scanning optics 330). In some variations the entire first optical path may be separate from the second optical path. In some variations the first and second optical path may share one or more optical components. In FIG. 3A, the first and second optical path both include the mirror 319 so that the optical paths are emitted from a common exit region 317 of the wand.

Figure 3B:
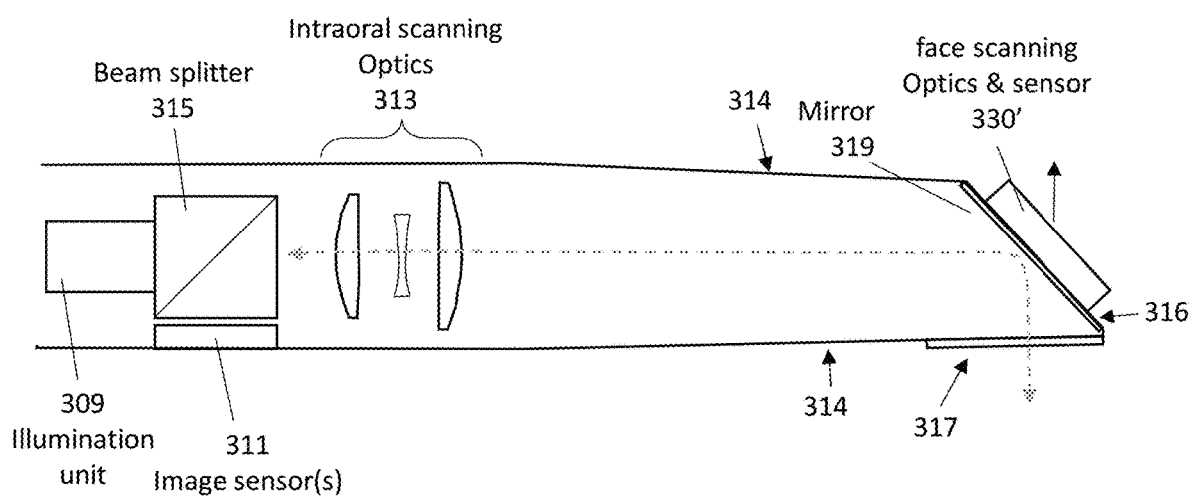
FIG. 3B shows another example of a view through a portion of an intraoral scanner configured to perform both intraoral scanning and facial scanning using the same wand.

Alternatively, in some variations, as shown in FIG. 3B, the second optical path, which is adapted for face scanning, may be entirely separate from the first optical path. For example, in FIG. 3B, the face scanning optics and a separate sensor 330' may be separately integrated into or on the wand, apparat from the first optical path. In some variations the scanning may be taken from a different direction than intraoral scanning, such as from a back or front of the wand; in FIG. 3B facial scanning may be taken from a direction on the back side 314 of the wand, while intraoral scanning is done from a front side 312 of the wand, e.g., out of the exit region 317. Alternatively in some variations the facial scanning may be taken from the distal end of the wand 316. The first optical path for intraoral scanning in the variation shown in FIG. 3B may be otherwise the same (or similar) to that shown in FIG. 3A. As mentioned, in some variations the first and second path may overlap, including within the wand.

In some variations the intraoral scanner may be configured for intraoral scanning using structured light, e.g., for three-dimensional scanning using structured light techniques and/or light-field technology. A pattern (static and/or time-varying) that may be used with any of these apparatuses and methods may be configured for providing structured light imaging by projecting the known pattern (e.g., spots, grids, lines, bars, e.g., horizontal bars, arrays, etc.) and analyzing the manner in the pattern deforms when striking the target surface(s). The apparatus may calculate the depth and surface information of the object(s) in the scene. Thus, any of these apparatuses may be configured as structured light 3D scanners. For example, the intraoral scanning may include structured light scanning. In some variations the wavelengths of light used may be different, and different patterns of light may be applied corresponding to the different wavelengths. For example, visible and/or infrared light may be used. Any of these apparatuses may be configured as "invisible" or "imperceptible" structured light apparatuses, in which structured light is used simultaneously or concurrently without interfering with imaging at different frequencies. For example, infrared light and visible light may be applied and detected at high (including extremely high) frame rates that alternate between two different patterns. The patterns may be complimentary or opposite (e.g., in which the dark regions in a first pattern are illuminated in the second pattern). Different wavelengths of visible light may be used instead or in addition to infrared light. In some variations, structured light may be used for facial imaging, and/or for both intraoral imaging and facial imaging, which may provide three-dimensional data that may be used to reconstruct the 3D surface and/or volume of the teeth and/or face.

Figure 4:
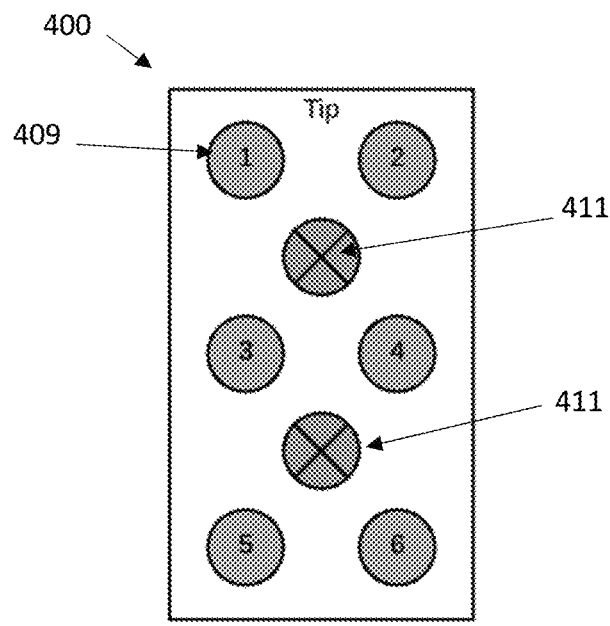
FIG. 4 is an example of an active region of an intraoral scanner (e.g., wand) that includes a plurality of sensors (e.g., sensor assemblies) and one or more light sources. The plurality of sensors show are numbered for conveniences, e.g., 409-1 to 409-6. More or fewer light sources (e.g., LEDs) may be include.

In some variation of the wand, including some variations adapted for use with structured light scanning, the sensor(s) (e.g., camera sensor(s)) may be positioned at or near the tip 337, rather than further within the wand body, as in the examples of FIGS. 3A-3B. For example, the sensor(s) and/or light sources may be positioned closer to the tip, and optics, such as lens (es) filter(s), etc. forming the optical path may be positioned immediately in front of the sensor(s) at or near the tip. For example, FIG. 4 shows one example of a distal tip region 400 (e.g., equivalent to the exit regions described in FIGS. 3A-3B) on the wand may include a plurality of sensor or sensor modules 409 (six sensor modules are shown in FIG. 4, 409-1 to 409-6). A sensor (or camera) may be part of a sensor module; the sensor module may include optical components (lenses, filters, etc.) forming the optical path. In FIG. 4, the sensor modules may each contain optical components, therefore parallel optical paths may be used, e.g., for intraoral scanning. Alternatively or additionally, in some variations a set of optical components, such as lenses, filters, etc., may be included and placed over all or a subset of the sensors or sensor modules. In FIG. 4, the tip region 400 may also include one or more illumination (e.g., light) sources 411 that may be configured to illuminate the teeth and/or face for imaging by the wand.

In some variations some of the sensor modules 409 may be configured to intraoral scanning (e.g., having a depth of focus for capturing teeth, such as between 1-20 mm) and some of the sensor modules (e.g., 409-5, 409-6) may be configured for facial scanning (e.g., having a depth of focus appropriate for capturing the face, such as between 20-200 mm). Thus, in one example of an apparatus having a sensor array similar to that shown in FIG. 4, the first optical path may include one or more sensors modules (e.g., sensor modules 409-1, 409-2, 409-3, 409-4) configured for intraoral scanning, and one or more sensor modules configured for facial scanning (e.g., sensor modules 409-5, 409-6). Alternatively, in some variations all of the sensor modules may be adapted for intraoral scanning (409-1 to 409-6) and a second optical path may be configured to adapt the first optical path(s) of these sensor modules for facial scanning.

In both FIGS. 3A and 3B, the wand (including, in some variations such as that shown in FIG. 1B, the scanning portion and/or the handle portion in an integrated handle) may including both the first and second paths as part of the (e.g., integrated with) the wand, in some variations, as described in greater detail below, the second path may be part of a sleeve, cover, attachment, etc. that may be removably placed onto the wand and used for scanning. The second optical path may adapt the first optical path so for facial scanning, including adjusting the depth of focus.

Figure 5A:
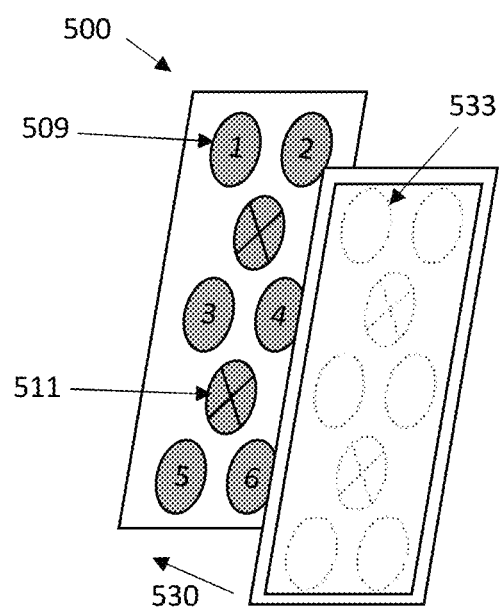
FIG. 5A is an example of a second optical path, which is configured to adapt a first optical path from an intraoral scanning mode to a facial scanning mode.

For example, FIG. 5A shows an example of a second optical path 533 that may be placed over the first optical path(s) of the wand to adapt the first optical path(s) 509 (509-1 to 509-6) for facial scanning. Each scanning module may include separate optical components, or optical components forming the second optical path may be shared. The illumination sources 511 may be unmodified or modified (e.g., filtered, etc.) by optical components. In FIG. 5A the second optical path may be paled over 530 the first optical path by attaching them to the wand, as part of a sleeve, cover, adapter, or the like. Alternatively, in some variations the wand may include the second optical path components as part of the wand, and may include a control for sliding or moving the second optical path over or into the first optical path. For example, the second optical path may be housed on the wand and slid over the distal tip region.

Figure 5B:
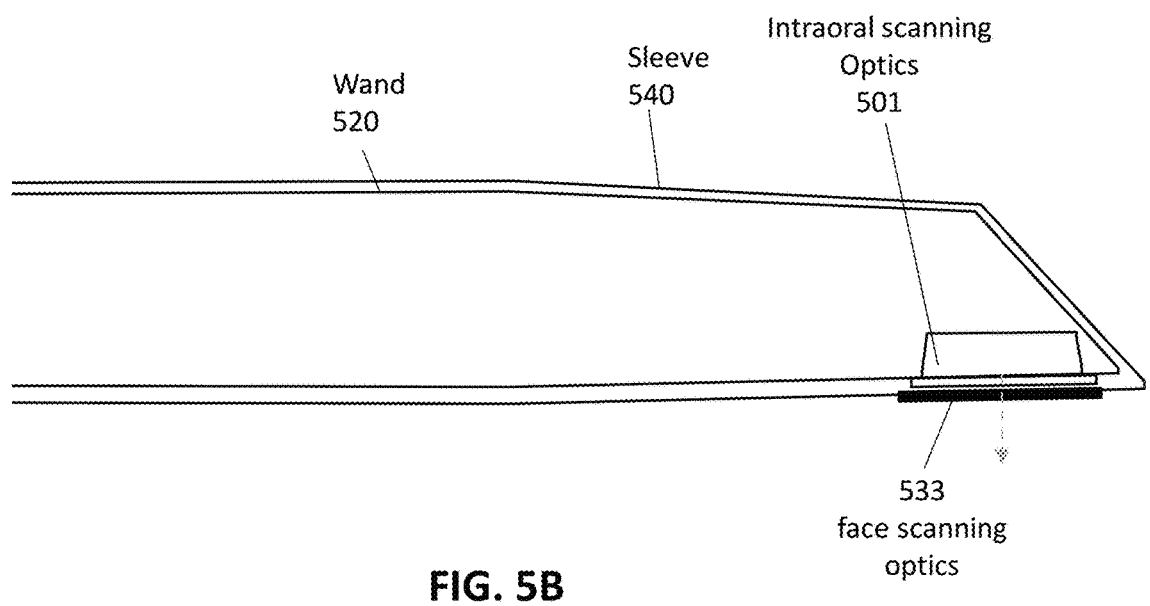
FIGS. 5B and 5C are schematic examples of views through a portion of an intraoral scanner configured for intraoral scanning, on which a sleeve that is configured to adapt the intraoral scanner to perform facial scanning using the same wand.

FIG. 5B illustrates one example of a wand 520 having a first optical path for intraoral scanning (e.g., including intraoral scanning optics 501, such as one or more scanning modules) at the distal tip region and a sleeve 540 that includes a second optical path 533 for facial scanning. A light source (illumination source, not shown) may also be provided for intraoral scanning. The second optical path may include optical components that adapt the first optical path(s) for from intraoral scanning to face scanning. The sleeve may be configured to fit over the wand or a portion of the wand. The fit between the sleeve and the wand may be snug so that the second optical path is coupled to the first optical path. In some variations the sleeve (or cover, adapter, etc.) may be secured by an attachment such as a snap, clasp, etc.; in some variations the sleeve (or cover, adapter, etc.) may be secured by a friction fit. The sleeve, attachment, cover, etc. may including an indicator indicating that it is properly attached. The indicator may be visible (e.g., a color indicator, etc.) audible, tactile, etc. (a click, snap, etc.). In any of the apparatuses described herein a contact or connection indicator may be included to indicate contact or connection between the wand and a sleeve, which may allow detection of the sleeve by the system. For example, connection or contact indicator may include an electrical contact, a magnetic contact, a capacitance detector, etc. to allow detection of the sleeve by the system.

Figure 5C:
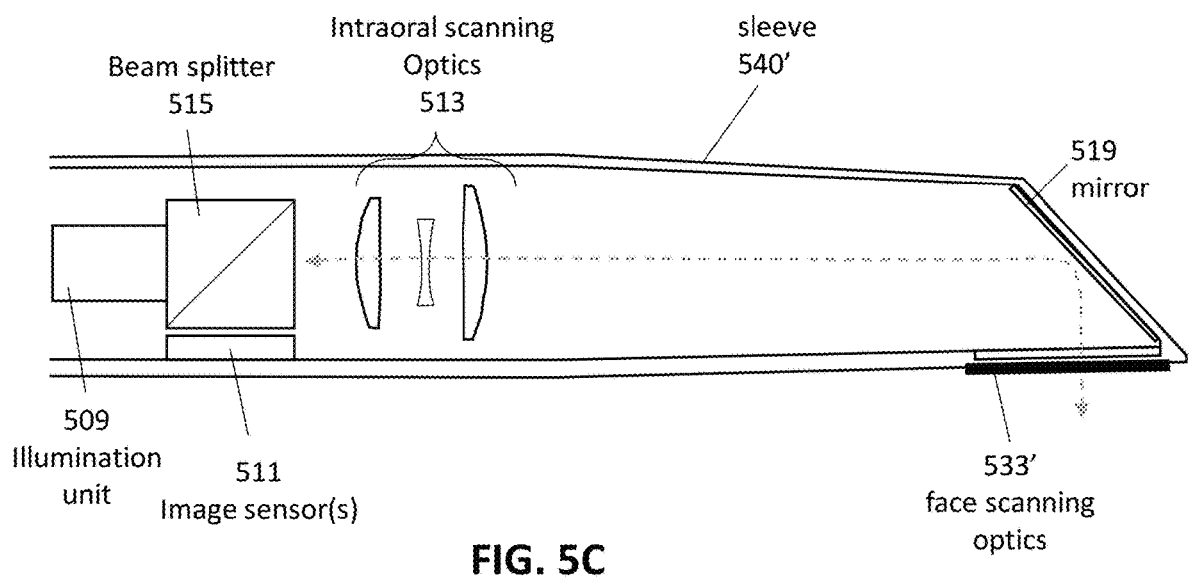

FIG. 5C shows another example of a sleeve 540' that is configured to adapt alternative intraoral scanning optics 513 (e.g., lenses, mirror 519, beam splitter 515, etc.), by including a second optical path that adapts the intraoral scanning optics into face scanning optics 533, as shown. In FIGS. 5B and 5C the sleeves may be configured to include one or more additional illumination sources for face scanning (not shown).

Figure 6A:
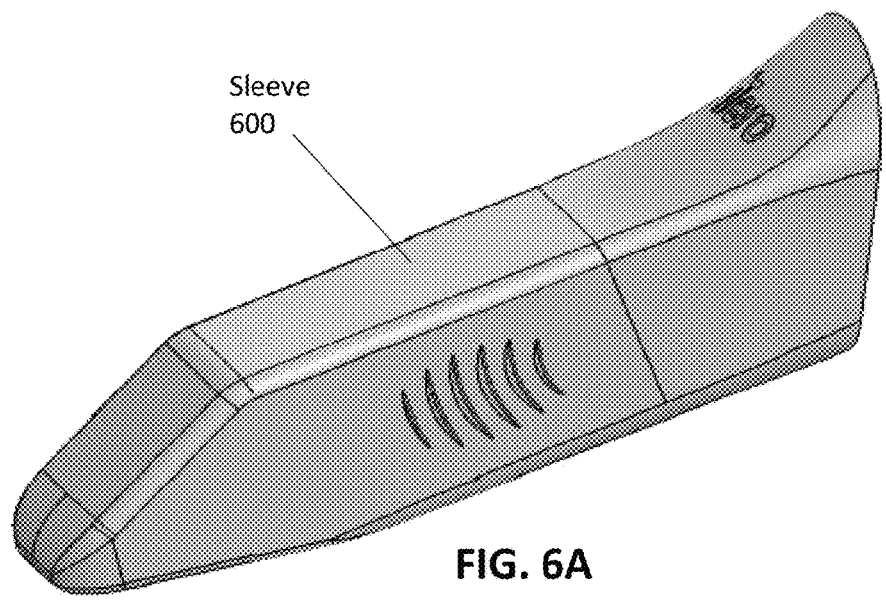
FIGS. 6A-6C illustrate one example of a sleeve that is configured to be attached to a wand.
Figure 6B:
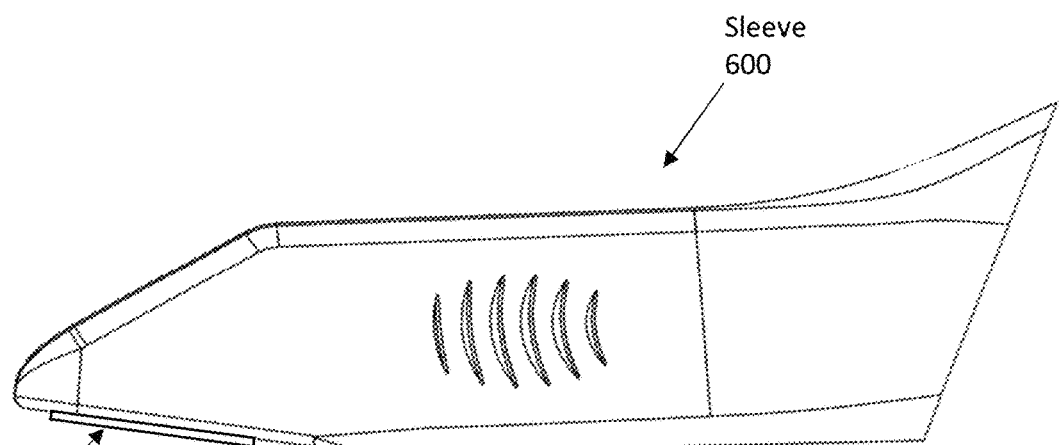
Figure 6C:
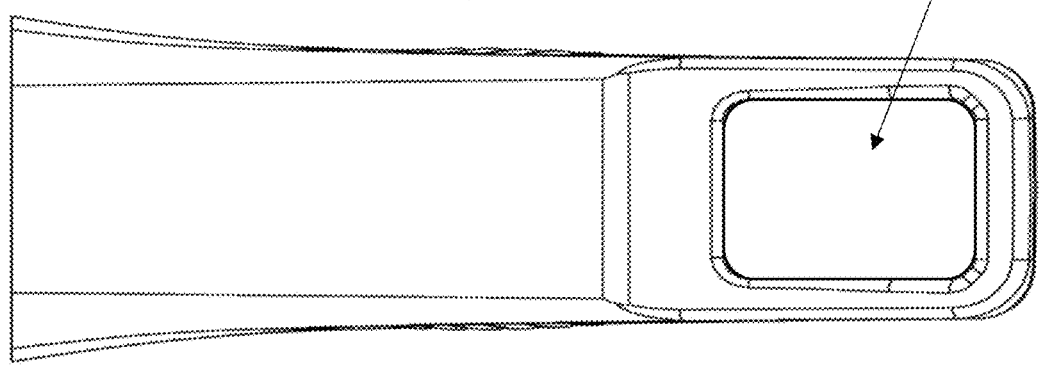

FIGS. 6A-6C illustrate another example of a sleeve that may include optics configured to adapt the optics of a wand from intraoral cavity scanning (e.g., having a focus of between 1-40 mm, e.g., between 1-30 mm, between 1-20 mm) to facial scanning (e.g., having a depth of focus of between 20-200 mm, between 30-200 mm, between 40-200 mm, between 40-100 mm, etc.). In FIG. 6A the sleeve 600 is shown from a top perspective view. The sleeve may include a second optical path 603 that is configured as adaptive optics for face scanning, as described above. In FIG. 6B the second optical path is shown and may cover (and be placed in tandem/in line with) the first optical path of a wand. FIG. 6C shows a bottom view, showing the second optical path 603.

As mentioned in some variations the apparatuses described herein may be configured for use with a Multi structured light (MSL) scanner for 3D scanning. In some variations these apparatuses may be configured as multi-use, add-on, sleeves that allow the MSL (Multi Structured Light) wand tip to capture a subject's face in 3D, as part of a complete "smile" design flow. The 3D capture can be based on passive stereo imaging (white light) or active structured light (laser based).

In any of the variations described herein, the apparatus may include calibration targets. For example, in some variations the sleeve, which may include the second optical path for adapting a first (intraoral) optical path, may also include calibration target(s) for the main MSL functions of the tip.

In some variations the wand may be configured to capture in 2D and 3D the intraoral cavity. As mentioned, this may mean that the want includes optics configured to image at a depth of capture in the range of about 1-40 mm (e.g., about 2-40 mm, about 3-40 mm, about 4-40 mm, about 1-30 mm, about 1-20 mm, about 2-30 mm about 2-20 mm, about 3-30 mm, about 3-20 mm, about 4-30 mm, about 4-20 mm, etc.). Such optics are typically not be suitable to capture images of the subject face, which may require a depth of focus in the range of about 40-200 mm (e.g., about 20-200 mm, about 20-150 mm, about 20-100 mm, about 30-200 mm, about 30-150 mm, about 30-100 mm, about 40-150 mm, about 40-100 mm, etc.).

In variations in which the second optical path is in a sleeve, cover, etc., the sleeve may be configured to include optical elements (e.g., passive optical elements, or in some variations, active optical elements) to extend the imaging range to enable 3D capturing of the subject face. To extend the capture range, the second optical path may include add-on optics, which may function as short-sightedness eyeglasses, correcting the "near-sightedness" of the wand (e.g., the first optical path). The optic lens (or group of lenses) of the second optical path may transform the wand to a 3D facial capturing device, optimized for face capturing in close range.

In some variations, different types of optic lens (or group of lenses) can be used in conjunction with cameras or group of cameras. For example, one group of lenses can be optimized to scan the face and other group of lenses can be optimized to scan the visible teeth.

For example, the wand may include a plurality of (e.g., 5-6) full color cameras for purposes of the intraoral scanning. For capturing a scan of the subject's face (e.g., a 3D color face stereo capture), a plurality of cameras (e.g., two or more cameras) may be included, resulting in simple and low cost enhanced sleeve. In some variations, for better performance of 3D stereo reconstruction, the most distant camera pair is preferably used, e.g., for facial reconstructions. In some variations, one camera may be used to capture multiple 2D images. Post processing algorithms, such as SLAM (Simultaneous Localization And Mapping) may be used to construct a 3D model/image (with or without additional data such as IMU (Inertial Measurement Unit)). In some embodiments, one camera may be used in conjunction with structured light illumination, and the 3D data generation may be done as image processing, after the images are captured. In another embodiment, three or more cameras may be used to enhance the 3D capture quality.

Facial scanning may include, in some variations, facial 3D capture, and in some variations may use all or part of the scanner white light (WL) illumination for active 3D capture.

In some variations, the illumination may be a high-speed sequence of short flashes image captures each will low exposure, which may then be summed for low noise image. 3D facial capture may be done using available (e.g., ambient, clinical, user-provided) light or using the overhead dentist illumination lamp. Alternatively, as mentioned above, in some variations suitable illumination conditions may be achieved by including lighting in the intraoral scanner, e.g., LEDs, etc. Image processing algorithms may dynamically optimize the light conditions based on the cameras captured image. In some variations, some or all of the illuminating elements (possibly combined with the sleeve optics) may be used to generate a visible pattern on the subject's face to assist the user with positioning the wand in the optimal position and orientation. Available structured light illumination may be used for 3D facial capture. In some variations, where a sleeve, cover, adapter, etc. is used with a second optical path, the sleeve, cover, adapter, etc. may include additional lighting and/or modifications to the illumination and capturing optics.

In some variations the sleeve, cover, adapter, etc. with the second optical path may include passive or active 3D calibration targets to allow calibration of the 3D scanner and compensate for long term mechanical or optical deviations. In general, the methods and apparatuses, including sleeves configured to adapt the optical path, e.g., for facial scanning, ma be used for or with other 3D capture technologies. The implementation may be different, as the illumination and imaging method may be different but the concept of optically changing the depth of focus may be applicable.

Methods

Figure 7A:
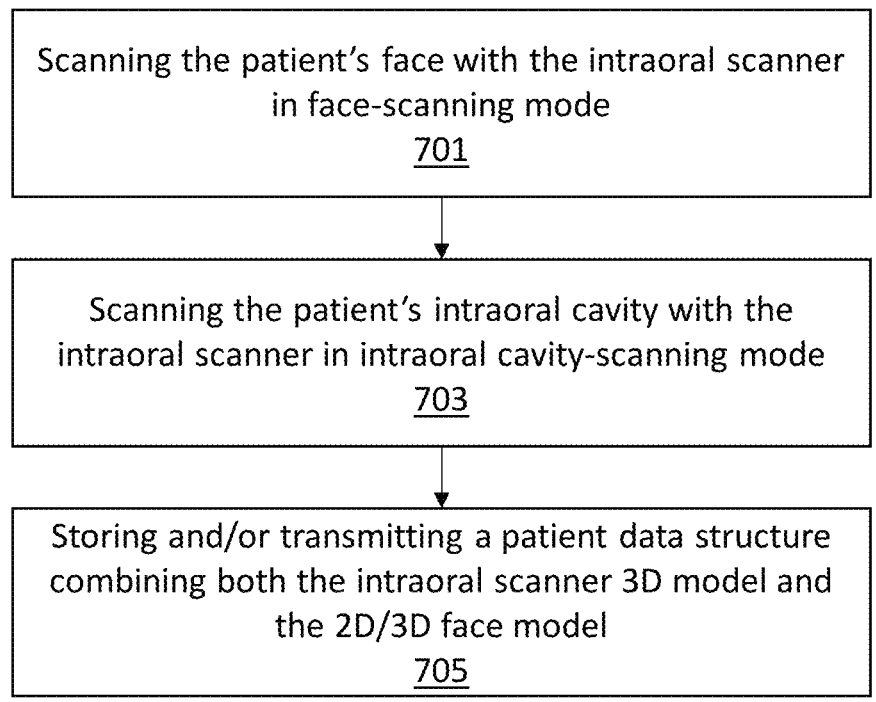
FIG. 7A is one example of a method scanning both a subject's face and the subject's dentition with the same wand apparatus as described herein.
Figure 7B:
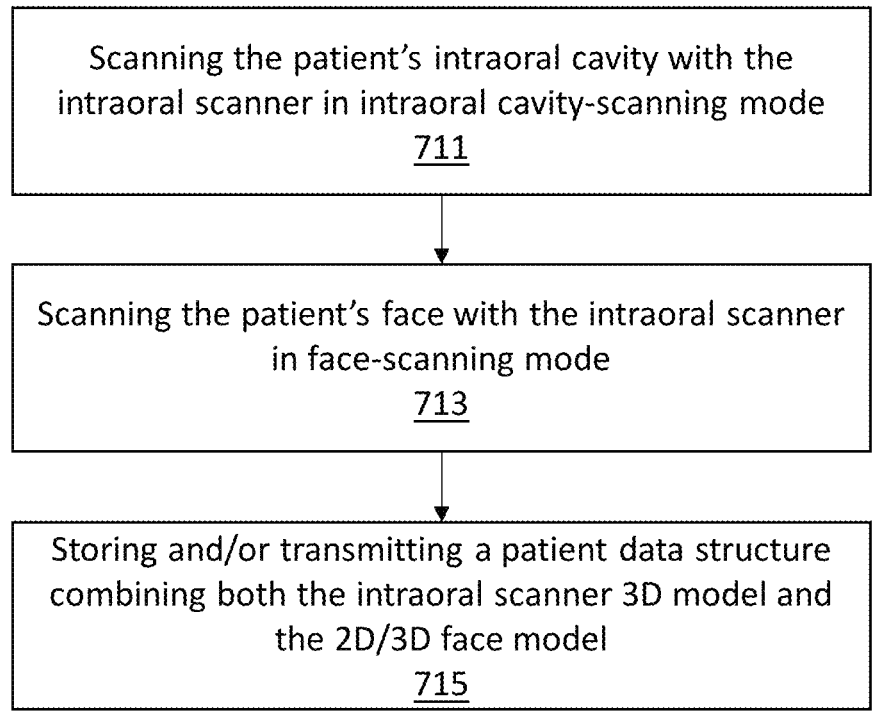
FIG. 7B is another example of a method of scanning both a subject's face and the subject's dentition with the same, e.g., wand of an intraoral apparatus, as described herein.

Also described herein are methods of scanning and/or modeling both a subject's intraoral cavity and/or, for example, FIGS. 7A and 7B schematically illustrate examples of methods of scanning both a subject's face and the subject's dentition with the same apparatus as described herein. For example, in FIG. 7A, the method may include first scanning the patient's face with an intraoral scanner in a first (e.g., face-scanning) mode 701. In FIG. 7A, once the intraoral scanner is used to scan within the subject's face, the same wand of the intraoral scanner may be used to scan the subject's mouth (intraoral cavity) 703. The user (e.g., dentist, technician, orthodontist, etc.) may operate a switch, control, toggle, etc. on or affiliated with the intraoral scanner, e.g., the handle portion of the wand, to switch between scanning the intraoral cavity at a first depth of focus to scanning in a face-scanning mode. The scan data for either or both scans (facial scans, intraoral scans, etc.) may be taken and stored by the intraoral scanner, either with or without additional processing. For example, in some variations these methods may include storing and/or transmitting a subject's digital scanning. The patient-specific data may be stored in a data structure that may combine both the intraoral scanning 3D (and therefore the 2D and/or 3D face model) 705. FIG. 7B shows an alternative in which the facial scanning may be performed after the intraoral scanning.

Any of the methods described herein may include methods of generating a digital model of both the intraoral cavity and the subject's face. For example, scanning both the face and the intraoral cavity may be scanned with an intraoral cavity scanning device. In some variations, the device can be configured for any scanning modality for the intraoral cavity: confocal, structured light, near-IR, ultrasound, etc. As mentioned above, the scanning may be 2D scanning or 3D scanning. In some variations the facial scanning may be done using the same intraoral scanner (e.g., same cameras/sensors and/or imaging sources, such as laser, light, etc., as for intraoral scanner, using adaptive optics to change the depth of focus) or in some variations a separate camera(s) on the scanner and/or a sleeve may be used.

In general, the facial scanning may be performed to scan in 2D or 3D. As mentioned, in some variations the face may be scanned using the same camera and/or imaging source: For example, a face may be scanned using different camera and imaging source: new optics on a sleeve, on wand, or protective sleeve etc. Can be on the end of the device top of the device/back, etc.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
   scanning a subject's face with an intraoral scanner; and
   scanning the subject's intraoral cavity with the same intraoral scanner,
   wherein scanning the subject's face with the intraoral scanner comprises passing light through a first optical path configured for intraoral scanning and a second optical path configured to adapt the first optical path for facial imaging.

2. The method of claim 1, wherein scanning the subject's face and scanning the subject's intraoral cavity are both scanned with the same one or more sensors.

3. The method of claim 1, further comprising removing a sleeve having face- scanning optics configured to extend the depth of focus of the intraoral scanner.

4. The method of claim 1, wherein scanning the subject's face with the intraoral scanner comprises scanning using a first one or more sensors on the intraoral scanner, further wherein scanning the subject's intraoral cavity comprises scanning using a second one or more sensors on the intraoral scanner.

5. The method of claim 1, wherein scanning the subject's face comprises scanning with a depth of focus of between 20 mm and 200 mm, and wherein scanning the subject's intraoral cavity comprises scanning with a depth of focus of between 2 mm-40 mm.

6. The method of claim 1, further comprising actuating a control on a wand of the intraoral scanner to switch between scanning the subject's face and scanning the subject's intraoral cavity.

7. The method of claim 1, wherein scanning the subject's face comprises forming a 3D image of at least a portion of the subject's face, and wherein scanning the subject's intraoral cavity comprises forming a 3D image of at least a portion of the subject's intraoral cavity.

8. The method of claim 1, wherein the subject's intraoral cavity is scanned before scanning the subject's face.

9. The method of claim 1, further comprising storing scan data from scanning of the subject's intraoral cavity with scan data from scanning the subject's face in a subject-specific data file.

10. The method of claim 1, wherein scanning the subject's intraoral cavity comprises scanning with structured light.

11. The method of claim 1, wherein scanning the subject's intraoral cavity comprises confocal scanning.

12. A method comprising:
scanning a subject's face with an intraoral scanner, wherein scanning the subject's face comprises passing light through a first optical path configured for intraoral imaging and a second optical path configured to adapt the first optical path for facial imaging; and
scanning the subject's intraoral cavity with the same intraoral scanner, wherein scanning the intraoral cavity comprises passing light through the first optical path but not the second optical path,
wherein the second optical path increases the depth of focus of first optical path.

13. The method of claim 12, further comprising removing a sleeve having optics comprising the second optical path before scanning the subject's intraoral cavity.

14. The method of claim 12, wherein the first optical path has a depth of focus of between 2 mm and 40 mm and the second optical path adjusts the depth of focus of the first optical path to be between 20 mm and 200 mm.

15. The method of claim 12, wherein scanning the subject's face comprises forming a 3D image of at least a portion of the subject's face, and wherein scanning the subject's intraoral cavity comprises forming a 3D image of at least a portion of the subject's intraoral cavity.

16. The method of claim 12, wherein the step of scanning the subject's intraoral cavity is performed before scanning the subject's face.

17. The method of claim 12, further comprising storing scan data from scanning of the subject's intraoral cavity with scan data from scanning the subject's face in a subject-specific data file.

18. The method of claim 12, wherein scanning the subject's intraoral cavity comprises scanning with structured light.

19. The method of claim 12, wherein scanning the subject's intraoral cavity comprises confocal scanning.

20. A method comprising:
scanning a subject's face with an intraoral scanner; and
scanning the subject's intraoral cavity with the same intraoral scanner, wherein scanning the subject's face is performed using a dedicated facial scanning sensor on the intraoral scanner that is separate from a sensor used for scanning the subject's intraoral cavity.

21. A method comprising:
scanning a subject's face with an intraoral scanner;
removing a sleeve having face-scanning optics configured to extend the depth of focus of the intraoral scanner; and
scanning the subject's intraoral cavity with the same intraoral scanner.

22. A method comprising:
scanning a subject's face with an intraoral scanner; and
scanning the subject's intraoral cavity with the same intraoral scanner,
wherein scanning the subject's face with the intraoral scanner comprises scanning using a first one or more sensors on the intraoral scanner, further wherein scanning the subject's intraoral cavity comprises scanning using a second one or more sensors on the intraoral scanner.

23. A method comprising:
scanning a subject's face with an intraoral scanner;
actuating a control on a wand of the intraoral scanner to switch between scanning the subject's face and scanning the subject's intraoral cavity; and
scanning the subject's intraoral cavity with the same intraoral scanner.

24. An intraoral scanner comprising:
a wand; and
a controller, comprising one or more processor and a non-transitory computer-readable storage medium storing a set of instructions capable of being executed by the processor, that when executed by the processor causes the processor to perform the steps of:
scanning a subject's face with the wand; and
scanning the subject's intraoral cavity with the same wand,
wherein scanning the subject's face with the wand comprises passing light through a first optical path configured for intraoral scanning and a second optical path configured to adapt the first optical path for facial imaging.

25. An intraoral scanner comprising:
a wand; and
a controller, comprising one or more processor and a non-transitory computer-readable storage medium storing a set of instructions capable of being executed by the processor, that when executed by the processor causes the processor to perform the steps of:
scanning a subject's face with the wand; and
scanning the subject's intraoral cavity with the same wand,
wherein scanning the subject's face is performed using a dedicated facial scanning sensor of the intraoral scanner that is separate from a sensor used for scanning the subject's intraoral cavity.

* * * * *